United States Patent [19]

Schamper

[11] 4,121,904

[45] Oct. 24, 1978

[54] DEPILATORY COMPOSITION FOR REMOVING HAIR FROM LIVE HUMAN SKIN

[75] Inventor: Thomas J. Schamper, Chicago, Ill.

[73] Assignee: Alberto-Culver Company, Melrose Park, Ill.

[21] Appl. No.: 735,741

[22] Filed: Oct. 26, 1976

[51] Int. Cl.$^2$ ............................................. A61K 7/155
[52] U.S. Cl. ..................................................... 8/161
[58] Field of Search .......................................... 8/161

[56] References Cited

U.S. PATENT DOCUMENTS

| | | | |
|---|---|---|---|
| 499,135 | 6/1893 | Mellinger | 8/161 |
| 1,982,268 | 11/1934 | Roth et al. | 8/161 |
| 2,352,524 | 6/1944 | Evans et al. | 8/161 |
| 2,823,168 | 2/1958 | Stonehill | 8/161 |
| 3,154,470 | 10/1964 | Braun | 8/161 |
| 3,194,736 | 7/1965 | Braun et al. | 8/161 |
| 3,426,137 | 2/1969 | Philpitt et al. | 8/161 |
| 3,527,559 | 9/1970 | Sliwinski | 8/161 |
| 3,981,681 | 9/1976 | de la Guardia | 8/161 |

*Primary Examiner*—Donald B. Moyer
*Attorney, Agent, or Firm*—Wallenstein, Spangenberg, Hattis & Strampel

[57] ABSTRACT

Depilatory compositions for removing hair from live human skin on the human body, said compositions containing, as essential ingredients, water; sodium thioglycolate and calcium thioglycolate, said thioglycolates representing the sole or essentially the sole depilating agents; a water-soluble soap, particularly sodium stearate, which is advantageously formed in situ by reaction of sodium hydroxide and a soap-forming aliphatic monocarboxylic acid, and ingredients which comprise a vehicle in the form of a cream or paste.

25 Claims, 1 Drawing Figure

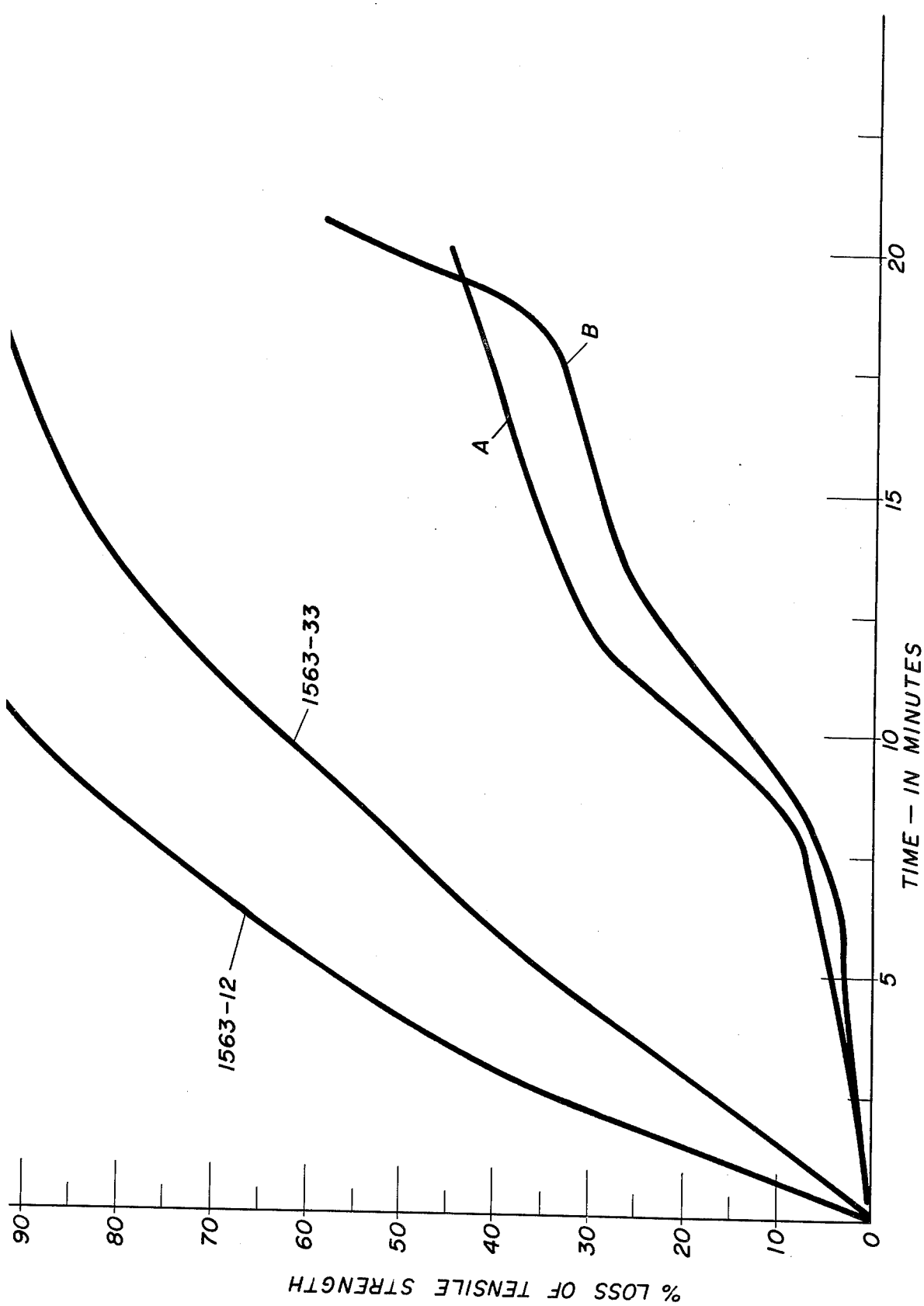

DEPILATORY COMPOSITION FOR REMOVING HAIR FROM LIVE HUMAN SKIN

The present invention relates to the production of thioglycolate depilatory compositions which are effective for the removal of hair from live human skin on the human body and which are characterized by improved properties over conventional presently known thioglycolate depilatory compositions, notably in regard to the speed at which they operate to effect removal of unwanted hair from the live human skin and without adverse effect on the non-irritative characteristics on the live human skin of the depilatory compositions. For convenience and simplicity, it will be understood that wherever hereafter the term "depilatory composition" is used in relation to the depilatories of the present invention, it will be understood to mean compositions for use on live human skin on the human body to effect the removal of unwanted hair.

Depilatory compositions for the removal of unwanted hair from live skin on the human body have long been known in which the active ingredient or ingredients include such compounds as, for instance, sulfides, polysulfides, hydrosulfides, stannites, thallium acetate and other thallium salts, various mercaptans, enzymes, and the like. Such as disclosed in various patents and publications, among which are, for instance, U.S. Pat. Nos. 1,379,855; 2,352,524; 2,988,485; 3,194,736; 3,271,258 and British Pat. No. 484,467. The advantages, as well as the disadvantages and objectionable features and properties of such depilatories, are well known to the art and require no elaboration.

The most commonly used depilatories, for removal of unwanted hair from live skin on the human body, at the present time and for many years past, are those which employ thioglycolates, particularly alkaline earth metal thioglycolates and especially calcium thioglycolate, it being common practice to utilize mixtures of calcium thioglycolate and sodium thioglycolate. Where thioglycolic acid is used in such formulations, it is conventional practice to neutralize it with alkaline earth metal hydroxides, most commonly calcium hydroxide or calcium hydroxide and sodium hydroxide. A slight excess of alkalinity is included to provide a reservoir of alkalinity, usually calcium hydroxide, for maintaining the alkalinity of the depilatory substantially constant at the pre-selected pH value desired, generally in the range upward of about 10 or, more commonly about 12 to 12.5. The foregoing are disclosed in the above-mentioned U.S. Pat. No. 2,352,524 and in various other publications. Such depilatories are most commonly marketed in the form of creams or pastes. On application to the skin on the human body and remaining thereon a short time, commonly about 5 to 10 to about 15 or 20 minutes or so, they effectively remove the unwanted hair, generally without irritation of the human skin, and are readily wiped or washed off, along with the degraded unwanted hair, with water or a stream of water or with a wetted cloth or the like.

The present invention is based upon certain discoveries which result in effectively improving the depilatories of the type which use alkaline earth metal thioglycolates such as calcium, magnesium and strontium thioglycolates, especially calcium thioglycolate, in admixture with sodium thioglycolate. The improvement resides essentially in increasing the speed of removal of the unwanted hair and, in certain cases, with an improvement in the gentleness of the compositions in relation to the human skin, or, in any event, not adversely affecting the non-irritation to the human skin properties of the depilatory composition. In short, said speed of unwanted hair removal is increased in the depilatory compositions of the present invention over conventional depilatories at the same time or essentially the same pH values of both, while, at the same time, the compositions, as to their gentleness on the human skin, are at least as good as present commercial thioglycolate depilatory compositions generally, and, in certain cases, are also improved in this respect.

Before discussing in detail the particular nature of the improved depilatory compositions of the present invention and the disclosures of illustrative embodiments thereof, it may be noted, as is well known to the art, that thioglycolic type depilatories operate by weakening or cleaving or destroying the disulfide bonds or linkages of the cystine molecules. This bond cleavage weakens the hair protein so that, when a sufficient number of these bonds have been broken, the degraded hair can be simply wiped or washed away. Any increase in the rate of the attack on the cystine disulfide bond structure will increase the rate of hair removal.

Table 1 below gives the scheme of the reaction by (A) neutral thiol group attack on the disulfide, and (B) thiol anion attack on the disulfide.

Table 1

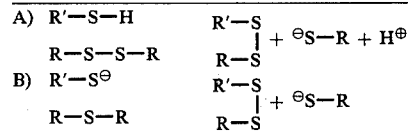

Both of the foregoing mechanisms involve nucleophilic attack on the disulfide bonds and the rate of cleavage increases with the nucleophilicity of the nucleophile. Scheme B will be the faster reaction because $R'-S^\ominus$ is a better nucleophile than $R'-SH$. Therefore, reaction conditions which will increase the concentration of $R'-S^\ominus$, the thiol anion, will increase the rate of cleavage of the disulfide bond.

Below is shown the equilibrium involved in the formation of dianion from the neutral species.

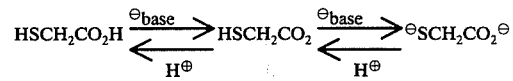

As can be seen from the equilibriums, increasing the concentration of the base will drive the equilibriums to the right. As is shown in Table 2, this can be accomplished by raising the pH.

Table 2

| |
|---|
| $pH = -\log[H^+]$ and |
| $[H^+][OH^-] = 10^{-14}$; thus |
| $pH = -\log \dfrac{10^{-14}}{[OH^-]} = -\log 10^{-14} + \log[OH^-]$ |
| $= 14 + \log[OH^-]$ |
| $pH - 14 = \log[OH^-]$ |

But it is also possible to raise the concentration of base in the equilibrium without significantly raising the pH. The above equations show that pH only measures the hydroxide ion concentration and not the total base concentration. Soaps, for instance, the sodium salt of stearic acid, drive the equilibrium to the right, increasing the nucleophilicity of the thioglycolic acid moiety.

The present invention, in its broader aspects, is predicated upon the discovery that by the inclusion of small proportions of sodium soaps of high molecular aliphatic monocarboxylic acids, notably $C_{12}-C_{22}$ aliphatic monocarboxylic acids, particularly $C_{16}-C_{18}$ fatty acids derived from animal and vegetable oils and fats, in paste or cream depilatory compositions containing alkaline earth metal thioglycolates together with sodium thioglycolate as the sole or essentially the sole or primary active depilating agents, the aforementioned improvements are obtained. In a more narrow, but highly valuable aspect of the present invention, the sodium thioglycolate is formed in situ by the interaction of sodium hydroxide and thioglycolic acid during the process of forming or producing the depilatory compositions of the present invention. Other features and aspects of the present invention will be pointed out in connection with following description and the illustrative working examples which describe the especially desirable embodiments of the invention.

The content of sodium thioglycolate and calcium thioglycolate, or other alkaline earth metal thioglycolate, in the depilatory compositions of the present invention is not critical except, of course, that they must be present in amounts sufficient to effect adequate depilation. The proportions thereof are consistent with proportions such as have heretofore been used in cream or paste depilatory compositions. Generally speaking, the sodium and calcium or other alkaline earth metal thioglycolates will usually each constitute from about 2 to 8%, preferably about 3 to 5%, based on the weight of the depilatory composition.

The proportions of the sodium soap in the depilatory compositions of the present invention are variable within reasonable limits but, generally speaking, they will usually fall within the range of about 2 to 8%, preferably 4 to 6%.

Where ingredients such as "PROMULGEN D" (Robinson-Wagner Co.), which is a self-emulsifier composition comprising more than about 50% of a mixture of cetyl and stearyl alcohols with from about 25% up to about 50% of an approximately 20 mole ethylene oxide adduct of a mixture of cetyl and stearyl alcohols, are used to produce the depilatory compositions in cream or paste form, the proportions thereof will generally fall within the range about 2 to about 8%, the amount thereof serving to control the consistency of the cream or paste.

In addition to the essential ingredients of the depilatory compositions of the present invention, namely, water; sodium thioglycolate; calcium thioglycolate (or other alkaline earth metal thioglycolate); a sodium soap of a soap-forming higher molecular weight aliphatic monocarboxylic acid; an ingredient or ingredients which result in a vehicle which provides the depilatory composition being in the form of a cream or paste, for instance the aforementioned "PROMULGEN D"; free sodium hydroxide and/or calcium hydroxide (or other alkaline earth metal hydroxide other than barium hydroxide) to produce a pH in the range of about 10 to about 12.5, the depilatory compositions of the present invention may, and most desirably do, contain various supplemental ingredients, generally in distinctly minor proportions. These include, by way of illustration, sequestrants such as sodium gluconate, sodium glucoheptonate and other known compounds which function as heavy metal scavengers and inhibit or prevent discoloration or the formation of colored bodies in the depilatory compositions; paraffin, petrolatum and mineral oils which, separately or together, serve to impart lubricating properties to the depilatory compositions; surfactants, coupling agents and emulsifiers which are utilized for their known properties in pastes and creams and certain of which also tend to impart a glossy appearance to the pastes and creams, which may be embodied in individual or separate compounds or in a single compound, and which are preferably of nonionic character, generally exemplified by ethoxylated or alkoxylated higher aliphatic alcohols or ethoxylated alkyl phenols, illustrative of which are 10 to 20 mole ethoxylated cetyl alcohols, 10-15 mole ethoxylated nonylphenols, and the like; perfumes or fragrances, etc. The proportions of the sequestrants may range generally from about 0.25 to about 2%, preferably about 0.5 to about 1%, the paraffin, petrolatum and mineral oils, either alone or mixtures of two or all of them, may range generally from about 2 to about 8%, preferably about 3 to 4%; the surfactants, coupling agents and emulsifiers may range, taken together, generally from about 0.5 to 5%, preferably about 1 to 2%; and the perfume or fragrances may range generally from about 0.25 to about 1.5%, preferably about 0.75 to 1.25%, all of the foregoing percentages being by weight of the finished depilatory composition.

In the particular advantageous procedure for preparing the depilatory compositions of the present invention, a dilute heated aqueous solution containing sodium hydroxide and the sequestrant, if utilized, is prepared, generally at a temperature in the range of about 150° to about 190° F. to facilitate the formation of the sodium soap and to aid in making the cream or paste emulsion although this temperature, while highly desirable, is not critical, and the situation is the same as to other temperatures referred to below. A separate heated mixture, generally in the same temperature range of about 150° to about 190° F., is prepared containing a cream-forming nonionic emulsifier such as a composition containing more than about 50% of a mixture of cetyl and stearyl alcohols and from about 25 to about 50% of an approximately 20 mole ethylene oxide adduct of a mixture of cetyl and stearyl alcohols (e.g. "promulgen D", Robinson-Wagner Co.), and the soap-forming aliphatic monocarboxylic acid such as stearic acid, the paraffin, petrolatum or mineral oil or mixtures thereof, if used. This second mixture is added to the first solution, under conditions of mixing or stirring, at a temperature within the aforementioned range, and for periods of time until a reasonably homogeneous composition is obtained, commonly in a period of about 20-45 minutes, depending upon the size of the batch and the mixing conditions. The resulting composition is then desirably cooled somewhat, commonly to a temperature in the range of about 80° to about 110° F., which results in a somewhat thickening of the emulsion, and an additional amount of sodium hydroxide is mixed in. A temperature rise generally occurs and the resulting mixture is again desirably cooled to within the aforesaid range of about 80° to about 110° F. to avoid any possible decomposition of the thioglycolic acid which is next to be added. Thioglycolic acid, in the desired amount, is then added, with stirring, which tends to cause a rise in temperature, and the batch is then desirably again cooled to bring it within the range of about 80° to about 110° F. and the perfume or fragrance, preferably in admixture with an emulsifier or surface active agent, is mixed in. Then calcium thioglycolate in the desired amount is added with good mixing or stirring to form a homogeneous composition in the form of a cream or paste which is then filled into suitable containers such as conventional tubes, jars or the like.

The following examples are illustrative of particularly preferred embodiments of the present invention. Other depilatory compositions can readily be prepared in light of the guiding principles and teachings disclosed above without departing from the spirit of the invention and which utilize the novel principles and concepts of the invention as more particularly pointed out in the claims. All parts given are by weight.

| Ingredients | Ex.I | Ex.II | Ex.III | Ex. IV | Ex.V |
|---|---|---|---|---|---|
| 1) Deionized Water | 70.82 | 70.05 | 67.82 | 67.82 | 67.82 |
| 2) Sodium Hydroxide (50% Active) | 2.8 | 2.8 | 2.8 | 2.8 | 2.8 |
| 3) Sodium Gluconate | 0.75 | 0.75 | 0.75 | 0.75 | 0.75 |
| 4) PROMULGEN D | 5 | 5 | 5 | 5 | 5 |
| 5) Stearic Acid, triple pressed | 4 | 4 | 4 | 4 | 4 |
| 6) Paraffin | 3 | 3 | 3 | — | — |
| 7) Petrolatum | — | — | — | 3 | — |
| 8) Mineral Oil | — | — | — | — | 3 |
| 9) Sodium Hydroxide (50% Active) | 3 | 5 | 6 | 6 | 6 |
| 10) Thioglycolic Acid (aqueous solution 80% active) | 4.63 | 3.4 | 4.63 | 4.63 | 4.63 |
| 11) PROCETYL AWS* | 1 | 1 | 1 | 1 | 1 |
| 12) Fragrance | 1 | 1 | 1 | 1 | 1 |
| 13) Calcium Thioglycolate | 4 | 4 | 4 | 4 | 4 |

*Ethoxylated cetyl alcohol (Croda Inc.)

The foregoing compositions may conveniently be prepared, in each of said Examples, in the following manner: Ingredients (1), (2) and (3) are mixed together and heated to about 170° F. Ingredients (4), (5), (6), (7) and (8) are admixed and heated to about 170° F. Then the latter mixture is added to the first mixture, with stirring, for about 30 minutes while maintaining the temperature of the mixture at about 170° F. The resulting batch is cooled to about 90° F. and ingredient (9) is added, with stirring. The resulting batch is again cooled to about 90° F. and ingredient (10) is added, with stirring. The batch is again cooled to about 90° F. and ingredients (11) and (12) are added, with stirring. Finally, ingredient (13) is added, with stirring, to form a homogeneous final product, which is in the form of a cream. It will be understood that variants in such mixing or formulating procedures can be utilized as will be apparent to those skilled in the art, particularly in light of the teachings provided above.

In use for removing unwanted hair on the live human skin, the depilatory compositions are applied and handled in the same way as heretofore known and currently marketed depilatory creams or pastes.

The attached drawing shows laboratory tests made, measuring loss of tensile strength of human hair against time, using two different depilatory compositions, in the form of creams, made in accordance with the present invention, and two different presently commercially marketed prior art cream depilatory compounds of third parties. The depilatory compositions designated 1563-12 and 1563-33 represent compositions made in accordance with the present invention, composition 1563-12 having a pH of 12.3, and composition 1563-33 having a pH of 11.8. Composition A had a pH of 12.0 and composition B had a pH of 12.2. It is apparent from the drawing that, in said laboratory test runs, compositions 1563-12 and 1563-33 act very distinctly more rapidly to bring about loss in tensile strength of human hair than do either of compositions A and B, despite the fact that the pH of composition 1563-12 is almost the same as that of composition B, and that the pH of composition 1563-33 is lower than that of either of compositions A or B. It may also be pointed out that, after neutralizing the free acids in the formulae of compositions 1563-12 and 1563-33, said compositions contained, respectively, 0.055 moles and 0.043 moles of extra hydroxide per 100 g of each of said compositions. Therefore, composition 1563-33 contained 22% less hydroxide than composition 1563-12, but composition 1563-33 still acted nearly as rapidly as composition 1563-12 despite the fact that the pH of composition 1563-33 was essentially half a unit lower than the pH of composition 1563-12.

The higher molecular weight aliphatic monocarboxylic acids whose sodium soaps are utilized in the production of the depilatory compositions include such acids as, for example, lauric acid, myristic acid, palmitic acid, stearic acid, oleic acid, ricinoleic acid, eleostearic acid, tallow fatty acids and mixtures of such higher molecular weight aliphatic monocarboxylic acids derived from animal and vegetable fats and natural or hydrogenated animal and vegetable oils. Especially satisfactory are the sodium soaps of normally solid fatty acids, particularly palmitic acid and stearic acid, and mixtures thereof as in triple pressed stearic acid.

While the sodium soaps which are utilized in the depilatory compositions of the present invention are produced in situ, as described above, in the process of preparing said depilatory compositions, in the broader aspects of the present invention preformed sodium soaps can be used and incorporated as such with the other ingredients to produce the depilatory compositions. However, the use of preformed soaps is distinctly less preferred because they tend to result in depilatory pastes or creams which are not as uniform, homogeneous and stable as those which are obtained when the procedure is followed where the sodium soaps are formed in situ.

It may be pointed out that, instead of utilizing sodium hydroxide in a total amount exceeding the stoichiometric amount necessary to react with the stearic acid or other higher molecular weight aliphatic monocarboxylic acid to form the soap, plus an excess thereover sufficient to impart a pH to the depilatory composition in the range of about 10 to about 12.5, variant procedures can be employed without departing from the principles and teachings of the present invention. Thus, for instance, the total amount of sodium hydroxide used may be substantially stoichiometrically sufficient to form the sodium soap, and an alkaline earth metal hydroxide, other than barium hydroxide, particularly calcium hydroxide, can be added to provide the alkalinity or alkaline reserve to provide the aforesaid pH value in the depilatory composition. Again, instead of using a preformed calcium thioglycolate in the preparation of the depilatory compositions of the present invention, thioglycolic acid can be used and neutralized with both sodium hydroxide and calcium hydroxide in appropriate proportions to form the sodium and calcium thioglycolates in the desired amounts, with a sufficient excess of sodium hydroxide or calcium hydroxide to provide a pH of about 10 to about 12.5 in the finished depilatory composition. In this general connection, it may also be observed that if, in the carrying out of the process for the preparation of the depilatory compositions of the present invention, all of the sodium hydroxide used in the formulations were used in the first step of the process, the stability of the emulsion comprising the finished cream or paste would be somewhat adversely affected. Hence, for best results, it is most advantageous that the sodium hydroxide be added in separate amounts in the different steps of the process as described in the best embodiments of the present invention as reflected by the working Examples. In the first step of the process the amount of sodium hydroxide utilized is substantially sufficient, or in slight excess thereover, to form the soap with the stearic acid, or other soap-forming higher aliphatic noncarboxylic acid utilized; and the second addition of the sodium hydroxide is in amount which serves mainly to convert the thioglycolic acid to sodium thioglycolate.

While the present invention is especially desirably practiced by utilizing, in the production of the depilatory compositions in cream or paste form, compositions such as the above-mentioned "PROMULGEN D", or other functionally equivalent self-emulsifier compositions which form, or aid in forming, the cream or paste, other non-depilating vehicles to provide or form a cream or paste can be utilized, as is per se well known to the art, such as, for instance, those containing colloidal clays, gums such as tragacanth and karaya, etc.

No novelty is claimed broadly in the use of soaps in compositions which have heretofore been used or suggested for use in depilatory compositions. Thus, in U.S. Pat. No. 1,379,855, reference is made to the use of metallic oxides, metallic hydroxides, metallic salts, paraffins or certain soaps to modify the transparency and consistency of sulfide and sulfhydrate depilatories; and, in U.S. Pat. No. 2,988,485, in depilatory compositions where the effective or essentially effective depilating agent is a proteolytic enzyme, bodying or bonding agents are disclosed in the form of various fatty alcohols, and examples of such agents which are recited are lauryl and cetyl alcohols, sodium stearate or myristate and soaps. These patents provide no concept or any suggestion whatever that sodium soaps such as sodium stearate have the property of speeding up the decrease in tensile strength of hair or increasing the speed of depilation when utilized in depilatory compositions in which the sole or essentially the sole depilating action is effected by thioglycolates, and particularly by mixtures of sodium and calcium thioglycolates.

The term "depilatory composition" as used in the claims means a composition which depends essentially for its hair removal effects on the presence of sodium thioglycolate and calcium thioglycolate and not on such extraneous ingredients as enzymes, sulfides, polysulfides, hydrosulfides, stannites, thallium acetate and other thallium salts, or such mercaptans as, for instance, ethyl mercaptan, propyl mercaptan and B-mercaptoaniline; and where the hair removal is effected by said thioglycolates at pH values at which thioglycolates are and heretofore have been known to function to bring about hair removal or depilation on the human body, namely, a pH in the range of about 10 to 12.5.

What is claimed is:

1. A process of preparing a cream or paste depilatory composition which comprises (a) providing a first heated dilute aqueous solution containing sodium hydroxide; (b) providing a heated second mixture containing (i) a cream or paste-forming nonionic surfactant, and (ii) a soap-forming $C_{12}-C_{22}$ aliphatic monocarboxylic acid; admixing said first solution and said second mixture; incorporating therewith an additional amount of aqueous sodium hydroxide and incorporating thioglycolic acid, under conditions of mixing, the total amount of sodium hydroxide being at least sufficient to form a soap with said monocarboxylic acid and to convert the thioglycolic acid to sodium thioglycolate; and adding an alkaline earth metal thioglycolate to produce a final composition having a pH in the range of about 10 to about 12.5.

2. The process of claim 1, in which the alkaline earth metal thioglycolate is calcium thioglycolate.

3. The process of claim 2, in which the (i) ingredient is a composition containing more than about 50% of a mixture of cetyl and stearyl alcohols and from about 25 to about 50% of an approximately 20 mole ethylene oxide adduct of a mixture of cetyl and stearyl alcohols.

4. The process of claim 2, in which the $C_{12}-C_{22}$ aliphatic monocarboxylic acid is at least one acid selected from the group of palmitic and stearic acids.

5. The process of claim 2, in which said first heated dilute solution also contains a sequestrant for heavy metals for inhibiting or preventing discoloration of said composition.

6. The process of claim 2, in which said heated second mixture contains at least one material selected from the group of paraffin, petrolatum and mineral oils.

7. A process of preparing a cream or paste depilatory composition which comprises (a) providing a first heated dilute aqueous solution of sodium hydroxide and a sequestrant for heavy metals; (b) providing a heated second mixture containing (i) a cream or paste-forming nonionic surfactant material, (ii) at least one fatty acid selected from the group of palmitic and stearic acids, and (iii) at least one material selected from the group of paraffin, petrolatum and mineral oils, incorporating therewith an additional amount of aqueous sodium hydroxide and incorporating thioglycolic acid, under conditions of mixing, the total amount of sodium hydroxide being at least sufficient to form a soap with the fatty acid and to convert the thioglycolic acid to sodium thioglycolate; and adding calcium thioglycolate to produce a final composition having a pH in the range of about 10 to about 12.5.

8. The process of claim 7, in which the (i) ingredient is a composition containing more than about 50% of a mixture of cetyl and stearyl alcohols and from about 25 to about 50% of an approximately 20 mole ethylene oxide adduct of a mixture of cetyl and stearyl alcohols.

9. A process of preparing a cream or paste depilatory composition which comprises (a) providing a mixture comprising a first dilute aqueous solution containing sodium hydroxide and sodium gluconate at a temperature of about 150–190° F., (b) providing a second mixture containing (i) a composition containing more than about 50% of a mixture of cetyl and stearyl alcohols and from about 25 to about 50% of an approximately 20 mole ethylene oxide adduct of a mixture of cetyl and stearyl alcohols, (ii) stearic acid, and (iii) at least one material selected from the group of paraffin, petrolatum and mineral oils, said second mixture being at a temperature of about 150°–190° F., admixing said first solution and said second mixture, reducing the temperature of the resulting mixture to in the range of about 80–110° F. and incorporating therewith, under conditions of mixing, an additional amount of aqueous sodium hydroxide, and adding thioglycolic acid, the first amount of sodium hydroxide being substantially sufficient or in slight excess over the amount required to react with the stearic acid to form sodium stearate, and the second amount of sodium hydroxide being sufficient itself or in conjunction with any excess in the first amount of sodium hydroxide to react with the thioglycolic acid to form sodium thioglycolate, and adding calcium thioglycolate to produce a final composition in the form of a cream or paste having a pH in the range of about 10 to about 12.5.

10. The process of claim 9, wherein the sodium stearate comprises from about 2 to about 8% by weight of the depilatory composition.

11. The process of claim 9, wherein the calcium thioglycolate comprises from about 2% to about 8% by weight of the depilatory composition.

12. The process of claim 9, wherein the sodium thioglycolate comprises from about 2% to about 8% by weight of the depilatory composition.

13. A cream or paste depilatory composition having a pH in the range from about 10 to 12.5 said composition containing a major proportion of water; and minor proportions of sodium thioglycolate, an alkaline earth metal thioglycolate as the active depilating agents, and a sodium soap of a $C_{12}$–$C_{22}$ aliphatic monocarboxylic acid, said composition having a greater speed of depilation than said composition without said soap.

14. A composition according to claim 13, in which the alkaline earth thioglycolate is calcium thioglycolate.

15. A composition according to claim 14, in which the sodium soap is a sodium soap of at least one fatty acid from the group of palmitic acid and stearic acid.

16. A composition according to claim 15, which contains also a sequestrant for heavy metals.

17. A composition according to claim 16, which contains a product containing more than about 50% of a mixture of cetyl and stearyl alcohols and from about 25 to about 50% of an approximately 20 mole ethylene oxide adduct of a mixture of cetyl and stearyl alcohols as a cream-forming and self-emulsifying agent.

18. A composition according to claim 17, which contains at least one material from the group of paraffin, petrolatum and mineral oils.

19. In a cream or paste depilatory composition which includes a major proportion of water; as the active depilatory ingredients, sodium thioglycolate and calcium thioglycolate; and free sodium hydroxide, to provide a composition having a pH in the range of about 10 to about 12.5, the improvement which comprises the inclusion in said composition of a sodium soap of a high molecular weight aliphatic monocarboxylic acid, said sodium soap comprising about 4 to about 6% by weight of said composition and serving to enhance the speed of depilation over that of said composition without said soap.

20. The composition of claim 19, in which the sodium thioglycolate constitutes from about 2 to about 8% and the calcium thioglycolate constitutes from about 2 to about 8% by weight of said composition.

21. The composition of claim 20, which also includes a sequestrant for heavy metals.

22. The composition of claim 21, which also includes at least one material from the group consisting of paraffin, petrolatum and mineral oils.

23. In a cream or paste depilatory composition containing a major proportion of water, sodium thioglycolate, calcium thioglycolate, and an excess of an alkaline reacting material in an amount sufficient to give the composition a pH in the range of about 10 to about 12.5, the improvement which comprises the inclusion in said composition of a sodium soap of a $C_{12}$–$C_{22}$ aliphatic monocarboxylic acid, said composition having a greater speed of depilation than said composition without said soap.

24. A composition according to claim 23, in which the $C_{12}$–$C_{22}$ aliphatic monocarboxylic acid is at least one acid selected from the group consisting of palmitic and stearic acids.

25. A composition according to claim 24, in which said sodium soap is formed in situ in said composition.

* * * * *